(12) United States Patent
Hartig et al.

(10) Patent No.: US 7,166,720 B2
(45) Date of Patent: Jan. 23, 2007

(54) PROCESS FOR THE PREPARATION OF α-AMINOSUBSTITUTED CARBOXYLIC ACID AMIDES

(75) Inventors: Thorsten Hartig, Bensheim (DE); Steffen Enke, Neckarhausen (DE)

(73) Assignee: Merck Patent Gesellschaft, Darmstadt (DE)

( * ) Notice: Subject to any disclaimer, the term of this patent is extended or adjusted under 35 U.S.C. 154(b) by 6 days.

(21) Appl. No.: 11/232,020

(22) Filed: Sep. 22, 2005

(65) Prior Publication Data

US 2006/0025587 A1 Feb. 2, 2006

Related U.S. Application Data

(62) Division of application No. 10/433,011, filed as application No. PCT/EP01/14519 on Dec. 11, 2001, now Pat. No. 7,053,211.

(30) Foreign Application Priority Data

Dec. 27, 2000 (DE) .............................. 001 28 232

(51) Int. Cl.
*C07D 225/04* (2006.01)
*C07D 487/00* (2006.01)
*C07D 491/00* (2006.01)
*C07D 215/20* (2006.01)
*C07D 215/36* (2006.01)

(52) U.S. Cl. ...................... 540/461; 540/523; 546/157; 546/158

(58) Field of Classification Search ................ None
See application file for complete search history.

(56) References Cited

U.S. PATENT DOCUMENTS

| | | | |
|---|---|---|---|
| 2,851,494 A | | 9/1958 | Erhart et al. |
| 4,619,784 A | | 10/1986 | Locatell, Jr. et al. |
| 5,977,355 A | * | 11/1999 | Urban .................. 540/523 |
| 6,262,068 B1 | | 7/2001 | Atwal et al. |

OTHER PUBLICATIONS

Hardman and Partridge, "Cyclic Amidines. Part VI.*5- and 7-Substituted 2-Amino-4-hydroxyquinolines" Journal of the Chemical Society, pp. 614-620 (1958).*
Tikk I et al., "Hydroxyiminoisoquinolin-3(2H)-ones, V: Synthesis of 4-Amino-1,2,3,4-tetrahydroisoquinolines," Acta Chimica Hungarica, 1986, pp. 255-262, vol. 121, No. 3, XP002207335, scheme 1, Akademiai Kiado, Budapest, HU.
Watthey J W H et al, "Synthesis and Biological Properties of (Carboxyalkyl)Amino-Substituted Bicyclic Lactam Inhibitors of Angiotensin Converting Enzyme," Journal of Medical Chemistry, 1985, pp. 1511-1516, vol. 28, No. 10, XP000942750 ISSN: 0022-2623 Cited in the application Schemata II and III, American Chemical Society, Washington, US.
Stjepan Kukolja et al, "Orally absorbable cephalosporin antibiotics. 2. Structure-activity studies of bicyclic glycine derivatives of 7-aminodeacetoxycephalospo ranic acid," Journal of Medical Chemistry, 1985, pp. 1896-1903, vol. 28, XP002126291 ISSN: 0022-2623 scheme III examples 6A, 13A, 14A, American Chemical Society, Washington, US.
Kägi H, "Über 7-Pyr-oxindol, 7-Pyr-isatin und 7,7'-Di-pyr-indigo," Helvetica Chimicata ACTA, 1941, pp. 141E-150E, vol. 24, XP002207336 examples IV, VI, VII.
Tikk I et al, "Hydroxyimino-3(2H)-isoquinolinones, II: A Convenient Method for the Preparation of 4-(Hydroxyimino)-1,4-dihydro-3(2H)-isoquinolinones and their o-Alkyl and o-Acyl Derivatives," Acta Chimica Hungarica, 1983, pp. 69-77, vol. 114, No. 1, XP002207337, p. 70, Akademiai Kiado, Budapest, Hu.
Beyer S K et al, "Notiz Zur Synthese Eines Optisch Aktives Ace-Hemmers Mit Amino-oxo-benzazepin-1-alkansaeure-struktu R Mittels Enantiokonvergierender, Kristallisationsinduzierter Racemat-tremung," Helvetica Chimica Acta, 1988, pp. 337-343, vol. 71, XP002207338, ISSN: 0743-7463 cited in the application scheme 1.
Watthey J W H et al, "Bicyclic Lactam Inhibitors of Angiotesin Converting Enzyme," Journal of Medical Chemistry, 1984, pp. 816-818, col. 1 examples 5A, 6, vol. 27, XP002217344.
Hino, Katsuhiko et al, "Agents acting on the central nervous system. Synthesis of 3-phenyl-2-piperazinyl-1-benzazocines, 3-substituted-2-piperazinyl-1-benzazepines and related compounds," Chem. Pharm. Bull (1988), 36(7), 2386-400' XP002217345 examples 12A, 12B.
Heinin J et al, "Hexahydro-5,6,6A,7,12,14 Isoquino2,3-Bbenzazepine-2 Nouvelle Voice D'Acces," Journal of Heterocyclic Chemistry, Jul. 1986, pp. 975-979, vol. 23, XP002917685 ISSN: 0022-152X examples 7A-7E, Heterocorporation, Provo, US.
Ito Y et al, "A New Synthetic Method for Preparation of 1,3,4,5-Tethrahydro-2H-1-Benzazepin-2-one Derivatitives," Chemistry Letters, 1980, pp. 487-490, XP001069799 ISSN: 0366-7022 examples 5A-III, Chemical society of Japan, Tokyo, Japan.
Henin, Jaques et al., "Reactivity in Alkaline Medium, of Nitrogen-containing Compounds with the Tetralone skeleton. I. Oxazolidines," Bull. Soc. Chim. FR. (1977), (1-2, PT. 2), 89-91, XP002217346 example 11A.

(Continued)

Primary Examiner—Zachary C. Tucker
(74) Attorney, Agent, or Firm—Millen, White, Zelano & Branigan, P.C.

(57) ABSTRACT

Hydroxy-imino derivatives of formula IIb are disclosed,

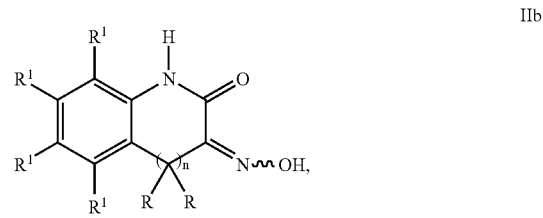

in which R and $R^1$ have the meanings given in the description.

4 Claims, No Drawings

OTHER PUBLICATIONS

Evans, D. et al., "The Schmidt Reaction with Aromatic Ketones," J. Chem. Soc. (Sep. 1965), 4806-12, XP002217347 example XIV.

Bauer, Ludwig et al, "The Semmler-Wolff Aromatization and Beckmann Rearrangement of 2-'B-(2-and-4-pyridyl)ethyll-1-tetralone oximes," J. Org. Chem. (1962), 27, 3982-5, XP002217348 example IX.

Jonnson and Mikiver, "Synthesis of 2-amino-3-(3,4-dihydroxyphenyl)-3-methylbutryic acid (beta, beta-dimethyl DOPA)" Acta Pharmaceutica Suecica, vol. 13(1), pp. 65-74 (1976).

Mukaiyama et al., "A Novel Method for the Preparation of Optically Active Dipeptide. Chemo- and Stereoselective Reduction of 2-Hydroxyimino AMides with Samarium Diodide" Chemistry Letters, vol. I, pp. 181-184 (1992).

Tikk et al., "Hydroxyimino-3(2H)-isoquinolineones, II" Acta Chimica Hungarica, vol. 114(I), pp. 69-77 (1983).

* cited by examiner

PROCESS FOR THE PREPARATION OF α-AMINOSUBSTITUTED CARBOXYLIC ACID AMIDES

This application is a divisional of application Ser. No. 10/433,011, now U.S. Pat. No. 7,053,211, filed 29 May 2003, under 35 U.S.C. 371, as the U.S. National Stage of PCT/EP01/14519, which was filed 11 Dec. 2001.

The invention relates to a general process for the preparation of α-aminosubstituted carboxylic acid amide compounds and/or their salts comprising reacting a carboxylic acid amide of a primary amine with a nitrosylating agent in the presence of a base followed by hydrolysis to give a hydroxy imino derivative followed by hydrogenation and if necessary converting a basic or acidic function of the α-aminosubstituted carboxylic acid amide into one of its salts.

The present invention relates therefore to a process for the preparation of α-aminosubstituted carboxylic acid amides of the formula III

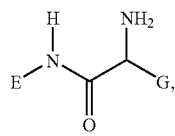

in which
E is a conjugated or an aromatic system and
G is a non-activating system
and their salts by direct nitrosylation of the corresponding unsubstituted carbamide of a primary amine of formula I

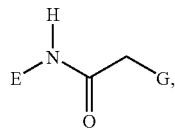

in which E and G have the meanings as indicated above in the presence of a base and reduction of the intermediates of formula II

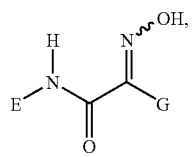

in which E and G have the meanings as indicated above and to special hydroxy imino derivatives of formula IIb and their follow up products of formula VIa as indicated below.

α-Aminosubstituted carboxylic acid amides are important intermediates in industrial organic synthesis, e.g. in the preparation of Life Science Chemicals such as fine chemicals, dyes, crop-protection compositions agrochemicals and/or pharmaceuticals. In one special aspect of the invention, compounds of formula IIIb as indicated below are important intermediates in the preparation of inhibitors of the angiotensin converting enzyme. In particular, 3-amino-1,3,4,5-tetrahydro-benzo[b]azepin-2-one is an intermediate in the synthesis of benazeprile, known from EP 72352.

It would be advantageous to prepare α-aminosubstituted carboxylic acid amides of primary amines from their corresponding unsubstituted carboxylic acid amides, because the unsubstituted carboxylic acid amides are readily and easily available.

From classical organic synthesis (see on this subject standard works on organic synthesis, such as Houben-Weyl, Methoden der organischen Chemie [Methods in Organic Chemistry], Georg-Thieme-Verlag, Stuttgart, or Beyer, Walter, Lehrbuch der organischen Synthese [Handbook of Organic Synthesis], S. Hirzel Verlag, Stuttgart), the N functionalisation at the α-position of carbamides of primary amines in the presence of a base, in particular of a carbamide of formula I as defined above, via direct nitrosylation is not known, if the methylene group in α-position of said carbamide is not activated by C=O, C≡N, N=C— or an aromatic carbocycle or heterocycle.

To the contrary, the N functionalisation at the α-position of carbamides of primary amines in the presence of an acid is known in the field of the art.

A. DeBruyn et al, Tetrahedron 1985, 41, 5553–55562 describes nitrosylation reactions with non-activated carbamides of secundary amines. These reactions are performed in the presence of a metal alcoholate, e.g. potassium tert-butylate in toluene.

By reacting non-activated carbamides of primary amines with tert-butylnitrit under the known reaction conditions, no oximation occurs.

Additionally, at date, methods of producing the special compounds of formula IIIb as indicated below as one special aspect of the invention via direct nitrosylation of unsubstituted carbamides of formula Ib as indicated below are unknown.

In one example, S. K. Boyer et al, Helv. Chim. Acta 1988, 71, 337f. describes the synthesis of 3-phthalimido-1,3,4,5-tetrahydro-benzo[b]azepin-2-one by reacting 3-bromo-1,3,4,5-tetrahydro-benzo[b]azepin-2-one, which is synthesized by bromination of 1-tetralone, followed by oximation and Beckmann rearrangement, with potassium phthalimide. Subsequent deprotection of the phthalimido protecting group according to known procedures e.g. by reaction with 2-aminoethanol would lead to 3-amino-1,3,4,5-tetrahydro-benzo[b]azepin-2-one.

In U.S. Pat. No. 4,873,235, W. H. Parsons et al. describes the synthesis of 3-amino-1,3,4,5-tetrahydro-benzo[b]azepin-2-one by reacting 3-bromo-1,3,4,5-tetrahydro-benzo[b]azepin-2-one, which is synthesized by bromination of 1-tetralone, followed by reaction with sodium azide to form 3-azido-1,3,4,5-tetrahydro-benzo[b]azepin-2-one. Subsequent hydrogenation of the azido group e.g. by reaction with sodium cyanoborohydride or in the presence of hydrogen on a suitable catalyst leads to 3-amino-1,3,4,5-tetrahydro-benzo[b]azepin-2-one.

Further common procedures for the preparation of compounds of formula IIIb as defined below, especially of 3-amino-3,4,5-tetrahydro-benzo[b]azepin-2-one are described in:

H. U. Blaser, S. K. Boyer, U. Pittelkow, *Tetrahedron: Asymmetry* 1991, 2, 721.

J. L. Stanton, J. W. H. Watthey, M. N. Desai, B. M. Finn, J. E. Babiarz, *J. Med. Chem.* 1985, 28, 1511.

G. B. Brown, V. S. Weliky, *J. Org. Chem.* 1958, 23, 125.

Th. K. Hansen, H. Thøgersen, B. S. Hanse, *Bioorg. Med. Chemistry Letters* 1997, 7, 2951.

J. D. Armstrong, III, K. K. Eng, J. L. Keller, R. M. Purick, F. W. Hartner, jr., W.-B. Choi, D. Askin, R. P. Volante, *Tetrahedron Letters* 1994, 35, 3239.

For economic and ecological reasons, the above cited known synthesis sequences are additionally disadvantageous for industrial application because on the one hand they use halogenated derivatives which are known to be extremely irritating and lachrymatory and stresses the environment or on the other hand they are multistage synthesis sequences.

The object of the invention was therefore to develop a simple process for the preparation of α-aminosubstituted carboxylic acid amides of primary amines.

Surprisingly, it has been found that direct nitrosylation of carboxylic acid amides of a primary amines in the presence of a strong base is possible to give hydroxy imino derivatives as intermediates which can be reduced to form the corresponding α-aminosubstituted carbamides according to the invention.

The process according to the invention is further advantageous because the hydrogenation reaction of the hydroxy imino derivatives can be easily carried out in the presence of an enantioselective catalyst to form enantiomers of said α-aminosubstituted carbamides.

The term E in a compound of formula I as defined above means a conjugated or an aromatic system which is able to stabilize a negative charge formed by deprotonation of a compound of said formula I. The term G in a compound of formula I as defined above means a non-activating system which is not able to stabilize a negative charge formed by deprotonation of a compound of said formula I.

The invention therefore provides in one aspect a process for the preparation of α-aminosubstituted carboxylic acid amides of the formula III

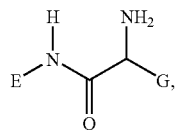

in which
E is selected from the group consisting of $R^1$—[(CR$^1$)=(CR$^1$)]$_n$—(CR$^1$)=(CR$^1$)—, in which
n is 0, 1, 2, 3, 4, 5, 6, 7, 8, 9, 10, 11, 12, 13, 14, 15, 16, 17, 18, 19, 20 or 21,
(CR$^1$) can be replaced by N and
R$^1$ independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, and t is 1, 2 or 3;

$R^1$—[(CR$^1$)=(CR$^1$)]$_n$—[C≡C]$_o$—[(CR$^1$)=(CR$^1$)]$_p$—, in which
n is 0, 1, 2, 3, 4, 5, 6, 7, 8, 9, 10 or 11,
o is 1, 2, 3, 4, 5, 6 or 7,
p is 0, 1, 2, 3, 4, 5, 6 or 7,
(CR$^1$) can be replaced by N and R$^1$ independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, and t is 1, 2 or 3;

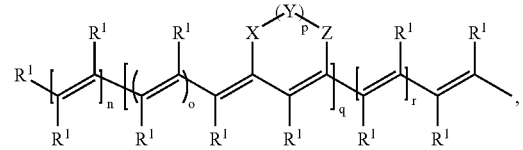

in which
n is 0, 1, 2, 3, 4, 5, 6, 7, 8, 9, 10 or 11,
o is 0, 1, 2 or 3,
p is 1, 2 or 3,
q is 1, 2 or 3,
r is 0, 1, 2, 3, 4, 5, 6 or 7,
X, Y and Z independently of each other are CH$_2$, NH, O or S, provided that X, Y and Z can not be alltogether a heteroatom,
(C—R$^1$) can be replaced by N,
and
R$^1$ independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, and t is 1, 2 or 3;

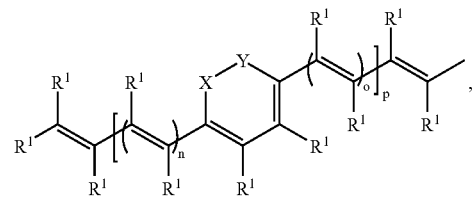

in which
n is 0, 1, 2, 3, 4, 5 or 6,
o is 0, 1, 2 or 3,
p is 1, 2 or 3,
X and Y independently of each other are CH$_2$, NH, O or S, provided that X and Y can not be alltogether a heteroatom,
(C—R$^1$) can be replaced by N,
and
R$^1$ independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, and t is 1, 2 or 3;
and
a mono- or polycyclic aromatic ring system having 0, 1, 2, 3 or 4 heteroatoms selected from the group consisting of N, O, and S wherein the ring nitrogen atoms are unsubstitued or substituted with one R$^2$ substituent and the ring carbon atoms are unsubstituted or substituted with one to five $R^1$ substituents and $R^1$ independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —$(CH_2)_t$—OA, Het, —$(CH_2)_t$—Het, —$(CH_2)_t$—OAr, Ar, OAr, O—$CH_2$—Ar, $NO_2$, NHA, $NA_2$, —$(CH_2)_t$—NHA, —$(CH_2)_t$—$NA_2$, COOH, COOA or CN, t is 1, 2 or 3 and $R^2$ can be H, A or CO-A;

G is selected from the group consisting of
H, A, —$(CR_2)_r$—OA, —$(CR_2)_r$—SA, cycloalkyl having 3 to 10 C atoms, —$(CR_2)_s$-cycloalkyl, fluoroalkyl having 1 to 3 C atoms, —$(CR_2)_r$—OAr, —$(CR_2)_r$—OHet, —$(CR_2)_s$—Ar, —$(CR_2)_s$—Het, NHA, $NA_2$, —$(CR_2)_s$—NHA or —$(CR_2)_s$—$NA_2$, R is independently selected from the group consisting of
H, A, —$(CH_2)_r$—OA, —$(CH_2)_r$—SA, cycloalkyl having 3 to 10 C atoms, —$(CH_2)_s$-cycloalkyl, fluoroalkyl having 1 to 3 C atoms, —$(CH_2)_r$—OAr, —$(CH_2)_r$—OHet, —$(CH_2)_s$—Ar, —$(CH_2)_s$—Het, NHA, $NA_2$, —$(CH_2)_s$—NHA or —$(CH_2)_s$—$NA_2$, r is 2, 3 or 4, s is 1, 2 or 3, A is alkyl having 1 to 10 C atoms, Ar is phenyl or naphthyl which are unsubstituted or mono- or disubstituted by A, OA or Hal, Hal is F, Cl, Br or I, Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, $CF_3$, $OCF_3$, $NH_2$, NHA, $NA_2$, COOH or COOA, and their salts, characterized in that (1) a compound of formula I

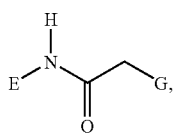

I in which E and G have the meanings as indicated above is reacted with nitrosyl tetrafluoroborate or a compound of formula IV

IV or a salt thereof, in which $R^3$ is OA, OAr, $OCH_2$—Ar or $Hal^1$,

A is alkyl having 1 to 8 C atoms,

Ar is phenyl or naphthyl which are unsubstituted or mono- or disubstituted by A, OA or Hal, $Hal^1$ is F or Cl, in the presence of a strong base followed by hydrolysis to give hydroxy imino derivatives of formula II

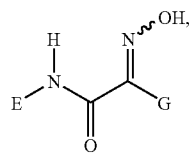

II in which E and G have the meanings as indicated above and in that (2) a compound of formula II is then hydrogenated and in that if necessary (3) a base or acid of the formula III is converted into one of its salts.

The invention therefore provides in another aspect a process for the preparation of α-aminosubstituted carboxylic acid amides of the formula III

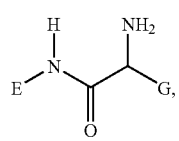

III in which

E and G together form a structural formula selected from the group consisting of

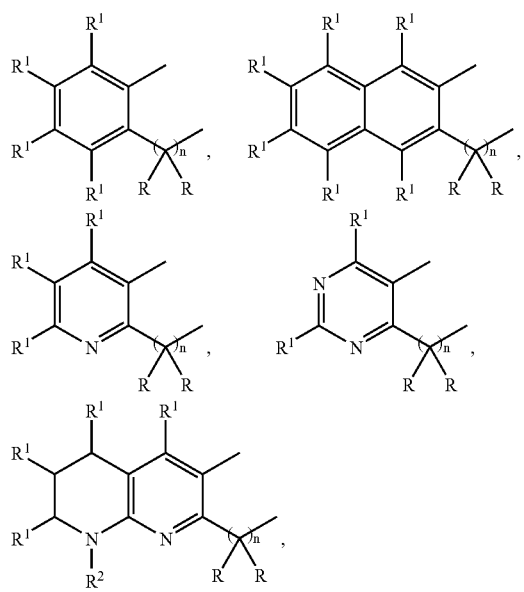

and in which

R is independently selected from the group consisting of H, A, —$(CH_2)_r$—OA, —$(CH_2)_r$—SA, cycloalkyl having 3 to 10 C atoms, —$(CH_2)_s$-cycloalkyl, fluoroalkyl having 1 to 3 C atoms, —$(CH_2)_r$—OAr, —$(CH_2)_r$—OHet, —$(CH_2)_s$—Ar, —$(CH_2)_s$—Het, NHA, $NA_2$, —$(CH_2)_s$—NHA or —$(CH_2)_s$—$NA_2$, $R^1$ is independently of each other H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —$(CH_2)_r$—OA, Het, —$(CH_2)_r$—Het, —$(CH_2)_r$—OAr, Ar, OAr, O—$CH_r$—Ar, $NO_2$, $NHA$, $NA_2$, —$(CH_2)_r$—NHA, —$(CH_2)_r$—$NA_2$, COOH, COOA or CN, $R^2$ is H, A or CO-A, r is 2, 3 or 4, s is 1, 2 or 3, t is 1, 2 or 3;

n is 1, 2 or 3,

A is alkyl having 1 to 8 C atoms,

Ar is phenyl or naphthyl which are unsubstituted or mono- or disubstituted by A, OA or Hal, Hal is F, Cl, Br or I, Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, $CF_3$, $OCF_3$, $NH_2$, NHA, $NA_2$, COOH or COOA, and their salts, characterized in that (1) a compound of formula I

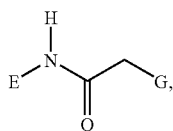
I in which E and G have the meanings as indicated above is reacted with nitrosyl tetrafluoroborate or a compound of formula IV

IV or a salt thereof, in which $R^3$ is OA, OAr, $OCH_2$—Ar or $Hal^1$, A is alkyl having 1 to 8 C atoms, Ar is phenyl or naphthyl which are unsubstituted or mono- or disubstituted by A, OA or Hal, $Hal^1$ is F or Cl, in the presence of a strong base followed by hydrolysis to give hydroxy imino derivatives of formula II

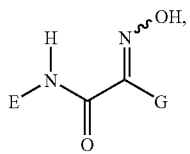
II in which E and G have the meanings as indicated above and in that (2) a compound of formula II is then hydrogenated and in that if necessary (3) a base or acid of the formula III is converted into one of its salts.

The abbreviations used have the following meanings:

Bu n-butyl t-Bu tert-butyl

Et ethyl

Me methyl

LDA lithium diisopropyl amide

THF tetrahydrofuran h hours

HPLC high pressure liquid chromatography

IPN isopropylnitrit

On account of their molecular structure, compounds of the formula III according to the invention can be chiral and can accordingly occur in various enantiomeric forms. They can therefore be present in racemic or in optically active form. The formula III includes all these forms.

The stereoisomeric forms can be separated into enantiomeric compounds by chemical, biochemical or physical measures known to the person skilled in the art, or even employed as such in the synthesis.

Thus diastereomers can be formed from the racemate of formula I by reaction with an optically active resolving agent. Suitable resolving agents for basic compounds of the formula I are, for example, optically active acids, such as the R and S forms of tartaric acid, diacetyl tartaric acid, dibenzoyltartaric acid, mandelic acid, malic acid, lactic acid, suitably N-protected amino acids (e.g. N-benzoylproline or N-benzenesulfonyl-proline) or the various optically active camphorsulfonic acids. Chromatographic resolution of enantiomers with the aid of an optically active resolving agent (e.g. dinitrobenzoylphenylglycine, cellulose triacetate or other derivatives of carbohydrates or chirally derivatized methacrylate polymers immobilized on silica gel) is also advantageous. Suitable eluents for this are aqueous or alcoholic solvent mixtures such as, for example, hexane/isopropanol/acetonitrile, e.g. in the ratio 82:15:3.

In the above or below formulae, A is alkyl and has 1 to 8, preferably 1, 2, 3, 4, 5 or 6 C atoms. Alkyl is preferably methyl, furthermore ethyl, propyl, isopropyl, butyl, isobutyl, sec-butyl or tert-butyl, additionally also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1-, or 2-ethylbutyl, 1-ethyl-1-methylpropyl, 1-ethyl-2-methylpropyl, 1,1,2- or 1,2,2-trimethylpropyl, heptyl or octyl. A is preferentially methyl, ethyl, propyl, isopropyl or tert-butyl. Particular preference is given to tert-butyl.

In the above or below formulae, Ar is phenyl or naphthyl, which is unsubstituted or mono- or di-substituted by A, OA or Hal.

Ar is preferentially phenyl, preferably 2-, 3- or 4-methylphenyl, 2-, 3- or 4-ethylphenyl, 2-, 3- or 4-propylphenyl, 2-, 3- or 4-isopropylphenyl, 2-, 3- or 4-butylphenyl, 2-, 3- or 4-tert-butylphenyl, 2-, 3- or 4-methoxyphenyl, 2-, 3- or 4-ethoxyphenyl, 2-, 3- or 4-pentoxyphenyl, 2-, 3- or 4-fluorophenyl, 2-, 3-or 4-chlorophenyl, 2-, 3- or 4-bromophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3-, 2,4-, 2,5-, 2,6-, 3,4- or 3,5-dimethoxyphenyl.

Phenyl is particularly preferred for Ar.

In the above or below formulae, cycloalkyl having 3 to 10 carbon atoms is preferably cyclopropyl, cyclobutyl, cyclopentyl, cyclohexyl, cycloheptyl or cyclooctyl. Cycloalkyl is likewise a monocyclic or bicyclic terpene, preferably p-menthane, menthol, pinane, bornane or camphor, where each known stereoisomeric form is included, or adamantyl. For camphor, this is both L-camphor and D-camphor.

In the above or below formulae, fluoroalkyl is preferentially mono-, di- or trifluoromethyl, 1- or 2-monofluoroethyl, 1,1-, 1,2- or 2,2-difluoroethyl, 1,1,2-, 1,2,2- or 2,2,2-trifluoroethyl, pentafluoroethyl, 3,3,3-trifluoropropyl or heptafluoropropyl. Particularly-preferred is trifluoromethyl.

In the above or below formulae, Hal is preferably F, Cl, Br or I.

In the above or below formulae, $Hal^1$ is preferably F or Cl.

In the above or below formulae, haloalkyl is preferentially mono-, di- or trifluoromethyl, 1- or 2-monofluoroethyl, 1,1-, 1,2- or 2,2-difluoroethyl, 1,1,2-, 1,2,2- or 2,2,2-trifluoroethyl, pentafluoroethyl, 3,3,3-trifluoropropyl or heptafluoropropyl, mono-, di- or trichloromethyl, 1- or 2-monochloroethyl, 1,1-, 1,2- or 2,2-dichloroethyl, 1,1,2-, 1,2,2- or 2,2,2-trichloroethyl, pentachloroethyl, 3,3,3-trichloropropyl or heptachloropropyl, mono-, di- or tribromomethyl, 1-or 2-monobromoethyl, 1,1-, 1,2- or 2,2-dibromoethyl, 1,1,2-, 1,2,2- or 2,2,2-tribromoethyl, pentabromoethyl, 3,3,3-tribromopropyl or heptabromopropyl. Particularly preferred is trifluoromethyl.

In the above or below formulae, haloalkoxy is preferentially mono-, di- or trifluoromethoxy, 1-or 2-monofluoroethoxy, 1,1-, 1,2- or 2,2-difluoroethoxy, 1,1,2-, 1,2,2- or 2,2,2-trifluoroethoxy, pentafluoroethoxy, 3,3,3-trifluoropropoxy or heptafluoropropoxy, mono-, di- or trichloromethoxy, 1-or 2-monochloroethoxy, 1,1-, 1,2- or 2,2-dichloroethoxy, 1,1,2-, 1,2,2- or 2,2,2-trichloroethoxy, pentachloroethoxy, 3,3,3-trichloropropoxy or heptachloropropoxy, mono-, di- or tribromomethoxy, 1- or 2-monobromoethoxy, 1,1- 1,2- or 2,2-dibromoethoxy, 1,1,2-, 1,2,2- or 2,2,2-tribromoethoxy, pentabromoethoxy, 3,3,3-tribromopropoxy or heptabromopropoxy. Particularly preferred is trifluoromethoxy.

In the above or below formulae, haloalkylthio is mono-, di- or trifluormethylsulfanyl, 1- or 2-monofluoroethylsulfanyl, 1,1-, 1,2- or 2,2-difluoroethylsulfanyl, 1,1,2-, 1,2,2- or 2,2,2-trifluoroethylsulfanyl, pentafluoroethylsulfanyl, 3,3,3-trifluoropropylsulfanyl or heptafluoropropylsulfanyl, mono-, di- or trichloromethylsulfanyl, 1- or 2-monochloroethylsulfanyl, 1,1-, 1,2- or 2,2-dichloroethylsulfanyl, 1,1,2-, 1,2,2- or 2,2,2-trichloroethylsulfanyl, pentachloroethylsulfanyl, 3,3,3-trichloropropylsulfanyl or heptachloropropylsulfanyl, mono-, di- or tribromomethylsulfanyl, 1- or 2-monobromoethylsulfanyl, 1,1-, 1,2- or 2,2-dibromoethylsulfanyl, 1,1,2-, 1,2,2- or 2,2,2-tribromoethylsulfanyl, pentabromoethylsulfanyl, 3,3,3-tribromopropylsulfanyl or heptabromopropylsulfanyl. Particularly preferred is trifluoromethylsulfanyl.

Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, $CF_3$, $OCF_3$, $NH_2$, NHA, $NA_2$, COOH or COOA.

Het is preferably 2- or 3-furyl, 2- or 3-thiophenyl, 1-, 2- or 3-pyrrolyl, 1-, 2-, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -4- or -5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3-, 4-, 5- or 6-2H-thiopyranyl, 2-, 3- or 4-4H-thiopyranyl, 3- or 4-pyridazinyl, pyrazinyl, 2-, 3-, 4-, 5-, 6- or 7-benzofuryl, 2-, 3-, 4-, 5-, 6- or 7-benzothienyl, 1-, 2-, 3-, 4-, 5-, 6- or 7-1 H-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 1-, 2-, 3-, 4-, 5-, 6-, 7- or 8-quinolinyl, 1-, 3-, 4-, 5-, 6-, 7- or 8-isoquinolinyl, 1-, 2-, 3-, 4- or 9-carbazolyl, 1-, 2-, 3-, 4-, 5-, 6-, 7-, 8- or 9-acridinyl, 3-, 4-, 5-, 6-, 7- or 8-cinnolinyl, 2-, 4-, 5-, 6-, 7- or 8-quinazolinyl. The heterocyclic radicals can also be partially or completely hydrogenated. Het can thus also be 2,3-dihydro-2-, -3-, -4- or -5-furyl, 2,5-dihydro-2-, -3-, -4- or -5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -3-pyrrolyl, tetrahydro-1-, -2- or 4-imidazolyl, 2,3-dihydro-1-, -2-, -3-, -4-, -5-, -6-, -7-1 H-indolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1,2,3,6-tetrahydro-1-, -2-, -3-, -4-, -5- or -6-pyridyl, 1-, 2-, 3- or 4-piperidinyl, 1-, 2-, 3- or 4-azepanyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolinyl, 1,2,3,4-tetrahydro-1-, -2-, -3-, -4-, -5-, -6-, -7- or -8-isoquinolinyl.

R is independently selected from the group consisting of H, A, $-(CH_2)_r-OA$, $-(CH_2)_r-SA$, cycloalkyl having 3 to 10 C atoms, $-(CH_2)_s$-cycloalkyl, fluoroalkyl having 1 to 3 C atoms, $-(CH_2)_r-OAr$, $-(CH_2)_r-OHet$, $-(CH_2)_s-Ar$, $-(CH_2)_s-Het$, NHA, $NA_2$, $-(CH_2)_s-NHA$ or $-(CH_2)_s-NA_2$, in which A, Ar, cycloalkyl, fluoroalkyl and Het have one of the above defined meanings and
s is 1, 2 or 3, preferentially 1.
r is 2, 3 or 4, preferentially 2.

R is preferentially H or A, particularly preferred H.

$R^1$ is independently selected from the group consisting of H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, $-(CH_2)_t-OA$, Het, $-(CH_2)_t-Het$, $-(CH_2)_t-OAr$, Ar, OAr, $O-CH_t-Ar$, $NO_2$, NHA, $NA_2$, $-(CH_2)_t-NHA$, $-(CH_2)_t-NA_2$, COOH, COOA or CN, in which A, Ar, cycloalkyl, fluoroalkyl, haloalkyl, haloalkoxy, haloalkylthio and Het have one of the above defined meanings and t is 1, 2 or 3, preferentially 1.

$R^1$ is preferentially H or A, particularly preferred H.

$R^2$ is independently selected from the group consisting of H, A or CO-A, in which A has one of the meanings as indicated above. $R^2$ is preferentially H.

$R^3$ is selected from the group consisting of OA, OAr, $OCH_2-Ar$ or $Hal^1$, where A, Ar and $Hal^1$ have a preferred meaning indicated beforehand. $R^3$ is preferentially butoxy, tert-butoxy, pentoxy, 3-methyl-but-1-yloxy or isopropoxy.

$R^4$ is selected from the group consisting of A, CO-A, $CH_2-Ar$, $(CH_2)_o-OA$, $-(CH_2)_o-Het$, $(CH_2)_o-OAr$, haloalkyl having 1 to 3 C atoms, $(CH_2)_o-NH_2$, $(CH_2)_o-NHA$ or $(CH_2)_o-NA_2$, where Ar, haloalkyl and Het have a preferred meaning indicated beforehand and o is 1, 2, 3, 4, 5, 6 or 7, preferentially 1.

$R^4$ is preferentially A, CO-A or $CH_2-Ar$, particularly preferably A.

E is independently selected from the group as defined in claim 2. E is particularly a mono- or polycyclic aromatic ring system having 0, 1, 2, 3 or 4 heteroatoms selected from the group consisting of N, O, and S wherein the ring nitrogen atoms are unsubstitued or substituted with one R² substituent and the ring carbon atoms are unsubstituted or substituted with one to five R¹ substituents, in which R¹ and R² have a meaning as indicated above.

Particularly preferred mono- or polycylic aromatic ring systems for E are pyridin-2-yl, naphthalen-1-yl and phenyl.

G is selected from the group consisting of H, A, —(CR$_2$)$_r$—OA, —(CR$_2$)$_r$—SA, cycloalkyl having 3 to 10 C atoms, —(CR$_2$)$_s$-cycloalkyl, fluoroalkyl having 1 to 3 C atoms, —(CR$_2$)$_r$—OAr, —(CR$_2$)$_r$—OHet, —(CR$_2$)$_s$—Ar, —(CR$_2$)$_s$-Het, NHA, NA$_2$, —(CR$_2$)$_s$—NHA or —(CR$_2$)$_s$—NA$_2$, where R, A, cycloalkyl, Ar and Het have a meaning as indicated above.

G is particularly preferred H or cyclohexyl.

E and G together form a structural formula selected from the group consisting of

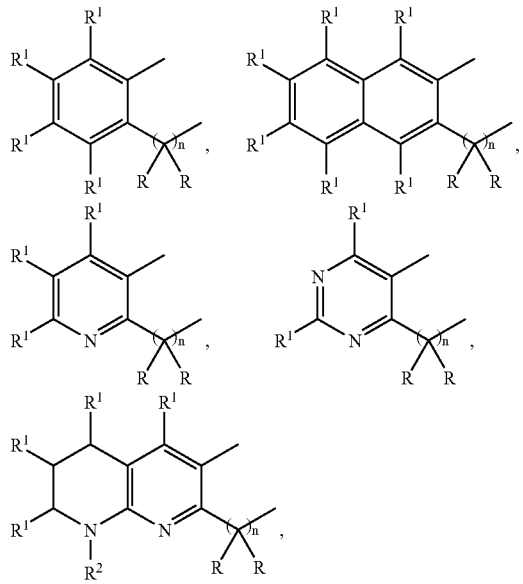

and in which R, R¹ and R² each independently have one of the above defined meanings and n is 1, 2 or 3.

E and G together form in particular the structural formula

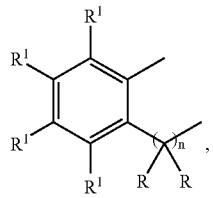

where R and R¹ each independently have one of the above meanings and n is 1, 2 or 3, particularly preferred R and R¹ are each independently H and n is 2.

In another aspect, the present invention is directed to a process for the preparation of compounds of formula III

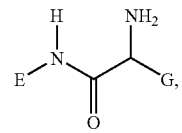

in which

E is a mono- or polycyclic aromatic ring system having 0, 1, 2, 3 or 4 heteroatoms selected from the group consisting of N, O, and S wherein the ring nitrogen atoms are unsubstitued or substituted with one R² substituent and the ring carbon atoms are unsubstituted or substituted with one to five R¹ substituents and R¹ independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, t is 1, 2 or 3, and R² can be H, A or CO-A;

G is selected from the group consisting of H, A, —(CR$_2$)$_r$—OA, —(CR$_2$)$_r$—SA, cycloalkyl having 3 to 10 C atoms, —(CR$_2$)$_s$-cycloalkyl, fluoroalkyl having 1 to 3 C atoms, —(CR$_2$)$_r$—OAr, —(CR$_2$)$_r$—OHet, —(CR$_2$)$_s$—Ar, —(CR$_2$)$_s$—Het, NHA, NA$_2$, —(CR$_2$)$_s$—NHA or —(CR$_2$)$_s$—NA$_2$, R is independently selected from the group consisting of H, A, —(CH$_2$)$_r$—OA, —(CH$_2$)$_r$—SA, cycloalkyl having 3 to 10 C atoms, —(CH$_2$)$_s$-cycloalkyl, fluoroalkyl having 1 to 3 C atoms, —(CH$_2$)$_r$—OAr, —(CH$_2$)$_r$—OHet, —(CH$_2$)$_s$—Ar, —(CH$_2$)$_s$—Het, NHA, NA$_2$, —(CH$_2$)$_s$—NHA or —(CH$_2$)$_s$—NA$_2$, r is 2, 3 or 4, s is 1, 2 or 3, A is alkyl having 1 to 10 C atoms, Ar is phenyl or naphthyl which are unsubstituted or mono- or disubstituted by A, OA or Hal, Hal is F, Cl, Br or I, Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF$_3$, OCF$_3$, NH$_2$, NHA, NA$_2$, COOH or COOA, and their salts, characterized in that (1) a compound of formula I

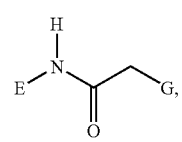

in which E and G have the meanings as indicated above is reacted with nitrosyl tetrafluoroborate or a compound of formula IV

or a salt thereof, in which
R³ is OA, OAr, OCH₂—Ar or Hal¹,
A is alkyl having 1 to 8 C atoms,
Ar is phenyl or naphthyl which are unsubstituted or mono- or disubstituted by A, OA or Hal,
Hal¹ is F or Cl, in the presence of a strong base followed by hydrolysis to give hydroxy imino derivatives of formula II

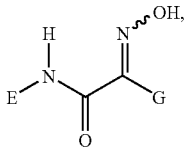

in which E and G have the meanings as indicated above and in that
(2) a compound of formula II is then hydrogenated and in that if necessary
(3) a base or acid of the formula III is converted into one of its salts.

In a preferred aspect, the present invention is directed to a process for the preparation of compounds of formula III

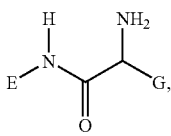

in which
E is pyridin-2-yl, naphthalen-1-yl or phenyl wherein the ring nitrogen atoms are unsubstitued or substituted with one R² substituent and the ring carbon atoms are unsubstituted or substituted with one to five R¹ substituents and
R independently can be H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH₂)$_t$—OA, Het, —(CH₂)$_t$—Het, —(CH₂)$_t$—OAr, Ar, OAr, O—CH$_t$—Ar, NO₂, NHA, NA₂, —(CH₂)$_t$—NHA, —(CH₂)$_t$—NA₂, COOH, COOA or CN,
t is 1, 2 or 3, and
R² can be H, A or CO-A;
G is selected from the group consisting of
H, A, —(CR₂)$_r$—OA, —(CR₂)$_r$—SA, cycloalkyl having 3 to 10 C atoms, —(CR₂)$_s$-cycloalkyl, fluoroalkyl having 1 to 3 C atoms, —(CR₂)$_s$—OAr, —(CR₂)$_r$—OHet, —(CR₂)$_s$—Ar, —(CR₂)$_s$—Het, NHA, NA₂, —(CR₂)$_s$—NHA or —(CR₂)$_s$—NA₂,
R is independently selected from the group consisting of H, A, —(CH₂)$_r$—OA, —(CH₂)$_r$—SA, cycloalkyl having 3 to 10 C atoms, —(CH₂)$_s$-cycloalkyl, fluoroalkyl having 1 to 3 C atoms, —(CH₂)$_r$—OAr, —(CH₂)$_r$—OHet, —(CH₂)$_s$—Ar, —(CH₂)$_s$—Het, NHA, NA₂, —(CH₂)$_s$—NHA or —(CH₂)$_s$—NA₂,
r is 2, 3 or 4,
s is 1, 2 or 3,
A is alkyl having 1 to 10 C atoms,
Ar is phenyl or naphthyl which are unsubstituted or mono- or disubstituted by A, OA or Hal,
Hal is F, Cl, Br or I,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF₃, OCF₃, NH₂, NHA, NA₂, COOH or COOA, and their salts, characterized in that
(1) a compound of formula I

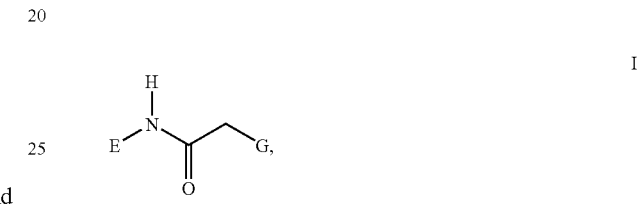

in which E and G have the meanings as indicated above is reacted with nitrosyl tetrafluoroborate or a compound of formula IV

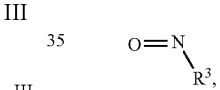

or a salt thereof, in which
R³ is OA, OAr, OCH₂—Ar or Hal¹,
A is alkyl having 1 to 8 C atoms,
Ar is phenyl or naphthyl which are unsubstituted or mono- or disubstituted by A, OA or Hal,
Hal¹ is F or Cl, in the presence of a strong base followed by hydrolysis to give hydroxy imino derivatives of formula II

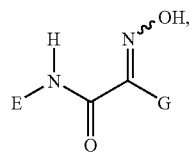

in which E and G have the meanings as indicated above and in that
(2) a compound of formula II is then hydrogenated and in that if necessary
(3) a base or acid of the formula III is converted into one of its salts.

Therefore, particularly preferred compounds of formula I, in which E and G do not together form a cyclic system, are the compounds selected from the following group:

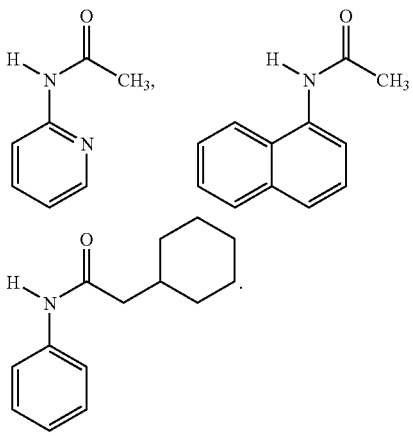

In another aspect, the present invention is directed to a process for the preparation of compounds of formula III,

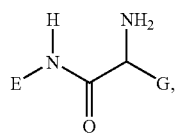   III in which E and G together form the structural formula

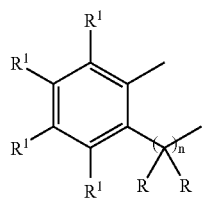

to generate a compound of formula IIIb

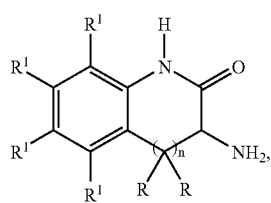   IIIb in which
R is independently selected from the group consisting of
  H, A, —(CH$_2$)$_r$—OA, —(CH$_2$)$_r$—SA, cycloalkyl having 3 to 10 C atoms, —(CH$_2$)$_s$-cycloalkyl, fluoroalkyl having 1 to 3 C atoms, —(CH$_2$)$_r$—OAr, —(CH$_2$)$_r$—OHet, —(CH$_2$)$_s$—Ar, —(CH$_2$)$_s$—Het, NHA, NA$_2$, —(CH$_2$)$_s$—NHA or —(CH$_2$)$_s$—NA$_2$,
R$^1$ is independentaly of each other H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN,
r is 2, 3 or 4,
s is 1, 2 or 3,
n is 1, 2 or 3,
t is 1, 2 or 3,
A is alkyl having 1 to 8 C atoms,
Ar is phenyl or naphthyl which are unsubstituted or mono- or disubstituted by A, OA or Hal,
Hal is F, Cl, Br or I,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF$_3$, OCF$_3$, NH$_2$, NHA, NA$_2$, COOH or COOA, and their salts, characterized in that
(1) a compound of formula Ib

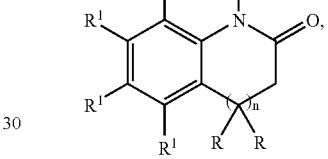   Ib in which R and R$^1$ each independently have the meanings as indicated above, is reacted with nitrosyl tetrafluoroborate or a compound of formula IV

   IV or a salt thereof, in which
R$^3$ is OA, OAr, OCH$_2$—Ar or Hal$^1$,
A is alkyl having 1 to 8 C atoms,
Ar is phenyl or naphthyl which are unsubstituted or mono- or disubstituted by A, OA or Hal,
Hal$^1$ is F or Cl, in the presence of a strong base followed by hydrolysis to give hydroxy imino derivatives of formula IIb

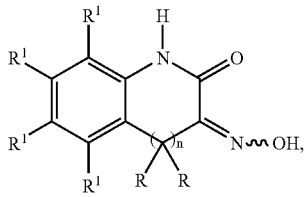   IIb in which R and R$^1$ each independently have the meanings as indicated above and in that (2) a compound of formula IIb is then hydrogenated and in that if necessary (3) a base or acid of the formula IIIb is converted into one of its salts.

In a preferred aspect, the present invention is directed to a process for the preparation of compounds of formula IIIb

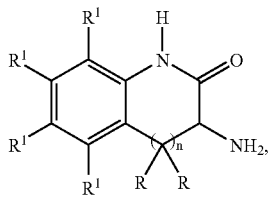

in which n is 2, that means compounds of formula IIIa

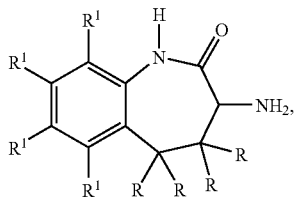

in which

R is independently selected from the group consisting of

H, A, —(CH$_2$)$_r$—OA, —(CH$_2$)$_r$—SA, cycloalkyl having 3 to 10 C atoms, —(CH$_2$)$_s$-cycloalkyl, fluoroalkyl having 1 to 3 C atoms, —(CH$_2$)$_r$—OAr, —(CH$_2$)$_r$—OHet, —(CH$_2$)$_s$—Ar, —(CH$_2$)$_s$—Het, NHA, NA$_2$, —(CH$_2$)$_s$—NHA or —(CH$_2$)$_s$—NA$_2$, R$^1$ is independentaly of each other H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, r is 2, 3 or 4, s is 1, 2 or 3, n is 1, 2 or 3, t is 1, 2 or 3, A is alkyl having 1 to 8 C atoms, Ar is phenyl or naphthyl which are unsubstituted or mono- or disubstituted by A, OA or Hal, Hal is F, Cl, Br or I, Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF$_3$, OCF$_3$, NH$_2$, NHA, NA$_2$, COOH or COOA, and their salts, characterized in that (1) a compound of formula Ia

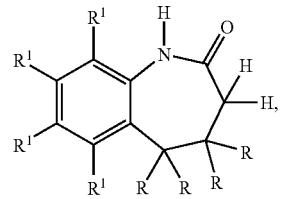

in which R and R$^1$ each independently have the meanings as indicated above is reacted with nitrosyl tetrafluoroborate or a compound of formula IV

or a salt thereof, in which

R$^3$ is OA, OAr, OCH$_2$—Ar or Hal$^1$,

A is alkyl having 1 to 8 C atoms,

Ar is phenyl or naphthyl which are unsubstituted or mono- or disubstituted by A, OA or Hal, Hal$^1$ is F or Cl, in the presence of a strong base followed by hydrolysis to give hydroxy imino derivatives of formula IIa

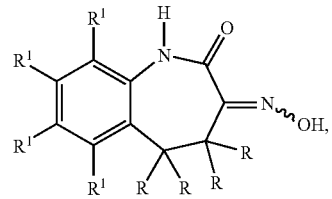

in which R and R$^1$ each independently have the meanings as indicated above and in that (2) a compound of formula IIa is then hydrogenated and in that if necessary (3) a base or acid of the formula IIIa is converted into one of its salts.

Therefore, particularly preferred compounds of formula I, in which E and G together form a cyclic system, is the compound 1,3,4,5-tetrahydro-benzo[b]azepin-2-one

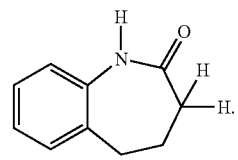

As a rule, the starting compounds of the formulae I, IV and V are known or commercially available.

The unknown compounds, however, can be prepared by methods known per se.

The substrates of formula Ib in which n is 1 can be prepared by reacting 2-nitro-trans-cinnamic acid wtih hydrogen in the presence of $PtO_2$ in the solvent acetic acid according to Sicker, D.; Rabe, A.; Zakrzewski, A.; Mann, G.; *J. Prakt. Chem.* 1987, 329; 1063–1070; or converting the corresponding ethyl ester unter similar conditions as described therein.

The substrates of formula Ib in which n is 2 (formula Ia) can be prepared by reacting 3,4-dihydro-2H-naphthalen-1-one oxime with polyphosphoric acid according to Nieduzak, Thaddeus R.; Boyer, Frederick E.; *Synth. Commun.* 1996 26; 3443–3452.

The substrates of formula Ib in which n is 3 can be prepared by reacting 6,7,8,9-tetrahydro-benzocyclohepten-5-one oxime according to Behringer; Meier; *Justus Liebigs Ann. Chem.* 1957, 607, 67, 83.

Compounds of formula Ib in which n is 0 can be prepared according to Houben-Weyl. Methoden der Organischen Chemie, Band XI/2, 560, 4. Aufl., Stuttgart, 1958.

The substrates of formula IV are mostly commercial available and can be prepared by reacting the corresponding alcohol with sodium nitrite in the presence of hydrochloric acid.

Preferred nitrosylating agents are pentyinitrit, 3-methyl-but-1-yl-nitrit, butylnitrit, tert-butylnitrit and nitsosyl chlorid or—tetrafluoroborate or, most preferably, iso-propylnitrit.

Any solvent can be used in the first stage of the process of the invention, that means the nitrosylation reaction, provided that it does not interfere with the formation of the hydroxy imino derivatives. Both polar aprotic or unpolar aprotic solvents and combinations thereof are acceptable. Suitable aprotic solvents are hydrocarbons such as hexane, petroleum ether, benzene, toluene or xylene, ethers such as dialkyl ether, diisopropyl ether, tetrahydrofuran or 1,3-dioxane, ethylene glycol dimethyl ether (diglyme) or diethyl ethylether, amides such as dimethylacetamide or dimethylfomamide (DMF), N-methyl pyrrolidone, dimethyl ethylene urea (DMEU), pyridine, or optionally also mixtures of the solvents mentioned with one another. A particularly preferred solvent in said nitrosylation reaction is tetrahydrofuran and 1,3-dioxane.

A suitable quantity of solvent typically ranges from about 5 to about 25 grams solvent per 100 gram reactant.

Non-limiting examples for suitable strong bases in the nitrosylation reaction of stage 1 of the process according to the invention are organo lithium reagents, combinations thereof or combinations together with alkali or alkaline earth metals, Grignard reagents, alkali metal alcoholates, alkali metal amides, alkali metal hydrides, alkaline earth metal hydrides, alkyl-, aryl- or arylalkylamines.

Examples of useful organo lithium reagents include lithium amide, lithium diisopropyl amide (LDA), lithium dimethylamide, methyllithium, n-butyllithium, sec-butyllithium, isopropyllithium, sec-amyllithium, n-hexyllithium, 4-heptyllithium, cyclopropyllithium or cyclohexyllithium, tert-butyllithium, tert-amyllithium, triethylmethyllithium, phenyllithium, 1-methylcyclopentyllithium or adamantyllithium.

Suitable bases for combination with organo lithium reagents as defined above are alkali or alkaline earth metals, such as sodium or potassium, Grignard reagents, such as MeMgBr, alkali metal alcoholates such as sodium methanolate, sodium ethoxide, potassium ethoxide, sodium isopropoxide, sodium tert-butoxide or potassium tert-butoxide, alkali metal amides, such as sodium amide, lithium hydride, alkali metal hydrides, such as sodium hydride, alkaline earth metal hydrides, such as calcium hydride, hydroxides such as sodium hydroxide or potassium hydroxide, alkyl-, aryl- or arylalkylamines, such as triethylamine, tributylamine, 1,8-diazabicyclo[5.4.0]-undec-7-ene or 1,8-diazabicyclo-[2.2.2]-octane. In the term "alkali metal" as used for the definition of said bases, the alkali metal lithium is excluded.

Preferably, the base is an organo lithium reagent or an organo lithium reagent in combination with alkali metal alcoholates, more preferably n-hexyllithium, n-butyllithium or tert-butyllithium or a combination of n-butyllithium, n-hexyllithium or tert-butyllithium with potassium tert.-butoxide.

The deprotonation with the aid of the strong base may be carried out additionally in the presence of complex builders, such as N,N,N,N,-tetramethyl-ethylene-diamine (TMEDA) or tetramethyl-piperidine.

Therefore, the invention further provides a process for the preparation of an aminosubstituted carboxylic acid amide in α-position according to claim 1, 12, 13 or 14, characterized in that the strong base be selected from the group consisting of organo lithium reagents, combinations thereof or combinations together with alkali or alkaline earth metals, Grignard reagents, alkali metal alcoholates, alkali metal amides, alkali metal hydrides, alkaline earth metal hydrides, hydroxides, alkyl-, aryl- or arylalkylamines.

Preferably, the molar ratio of strong base as single base or combination thereof to carbamide of the primary amine ranges from about 1,8:1 to about 5:1, and more preferably between about 2:1 and 4:1.

Preferably, in base mixtures, the molar ratio of organo lithium reagent to non-lithium base ranges from about 1:1 to about 4:1, and more preferably between about 2:1 and 3:1.

Therefore, the invention relates to a process according to claim 1, 12, 13 or 14, wherein the ratio of said base to said carboxylic acid amide of a primary amine is in the range of about 1.8:1 and 5:1.

Generally, the reagents in the nitrosylation reaction may be added to a solvent and mixed together in any order.

The reaction time of the nitrosylation reaction, depending on the conditions used, is between a few hours and 4 days.

The reaction temperature is between −150° and 10° C., preferably between −30° C. and −10° C. while adding the strong base to the unsubstituted carboxamide of primary amines. The reaction temperature of the nitrosylation reaction is between −30° C. and −20° C., preferably between −150° C. and 0° C.

Hydrolysis takes place while customary working up, as defined below to form crude hydroxy imino derivatives. Said oxime can be purified by conventional methods known to those skilled in the art, including, for example, chromatography or crystallization.

The conversion of hydroxy imino derivatives to α-aminosubstituted carboxylic acid amides is carried out according to the invention using electrochemical reduction, complex hydrides, such as $LiAlH_4$, $NaBH_4$, diborane, $NaAl(OCH_2CH_2OCH_3)_2H_2$ or combinations thereof with Lewis acids, hydrazine, combination of metals, such as iron or zinc, with acids, such as sulfuric acid, nitric acid, hydrohalic acids such as hydrochloric acid or hydrobromic acid, phosphoric acids such as orthophosphoric acid or sulfamic acid or hydrogen gas with the aid of a metal catalyst selected from the group consisting of Group 8 metals.

Suitable Lewis acids are $BF_3$, $AlCl_3$ or LiBr.

Therefore, the invention further provides a process according to claim 1, 12, 13 or 14, wherein said hydrogenation be carried out using electrochemical reduction, complex hydrides, hydrazine, combination of metals with acids or hydrogen gas with the aid of a metal catalyst selected from the group consisting of Group 8 metals.

Preferably, hydrogenation is carried out using hydrogen gas with the aid of a metal catalyst selected from the group consisting of Group 8 metals. Suitable catalysts are e.g. Raney nickel, palladium or platinum catalysts. Palladium or platinum catalysts may be present on supports, e.g. on charcoal, calcium carbonate, barium sulfate or strontium carbonate, in the form of oxides, such as platinum oxide, or in finely divided form. Hydrogenation can preferably be carried out under pressures of about 1 to 200 bar and at temperatures of about −80° to +150°. The hydrogenation is carried out in the presence of an inert solvent, for example an alcohol, such as methanol, ethanol or isopropanol, a carboxylic acid, such as acetic acid, an ester, such as ethyl acetate, or an ether, such as tetrahydrofuran or dioxane. It is also possible to use solvent mixtures, for example also mixtures which contain water. Hydrogenation under mild conditions, for example at temperatures of 0 to 50° and under pressures of about 1 to 5 bar is preferred.

Additionally, the hydrogenation reaction can be carried out using hydrogen gas in the presence of an enantioselective or an enantiomerically enriched catalyst to form enantiomers of formula I. Particularly preferably, the catalyst is a transition metal complex comprising a metal selected from the group rhodium, iridium, ruthenium and palladium, which is complexed with a chiral diphosphane ligand.

The ligands below may be mentioned by way of example:

(S)-EtDuphos:

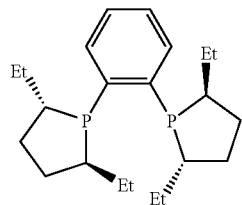

(S)-BINAP:

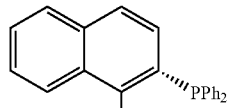

(S)-TolBINAP:

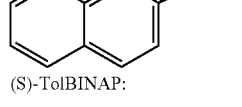

in which Tol is 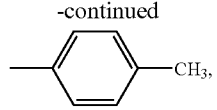 —CH$_3$, (S,S)-Chiraphos:

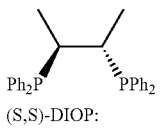

(S,S)-DIOP:

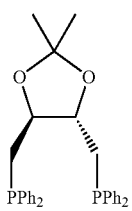

(S,S)-Skewphos (BDPP):

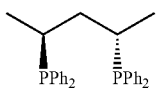

(S,S)-BPPM:

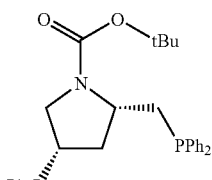

(R,R)-Norphos:

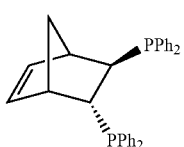

(S,R)-BPPFOH:

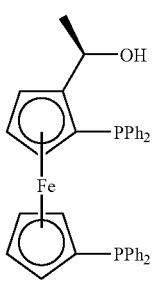

(S,R)-PFctBu:

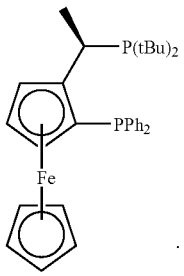

Depending on the choice of the (R) or (S) enantiomer of the ligand in the catalyst, the (R) or (S) enantiomer of formula I is obtained in an excess.

Precursors used for the chiral ligands are compounds such as, for example, Rh(COD)$_2$OTf (rhodiumcycloocatdiene triflate), [Rh(COD)Cl]$_2$, Rh(COD)$_2$BF$_4$, [Ir(COD)Cl]$_2$, Ir(COD)$_2$BF$_4$ or [Ru(COD)Cl$_2$]$_x$.

The reaction time of the enantioselective hydrogenation, depending on the conditions used, is between a few minutes and 14 days; the reaction temperature is between 0 and 150° C., normally between 20 and 130° C. Customarily, the catalyst/substrate ratio is between 1:2000 and 1:50, particularly preferably 1:1000 and 1:100. The reaction time is then, for example, between 3 and 20 hours. The hydrogenation is carried out under 1–200 bar of hydrogen, preferably at 3–100 bar.

Therefore, the invention further provides a process according to claim 1, 12, 13 or 14, wherein said hydrogenation be carried out using hydrogen gas in the presence of an enantioselective or an enantiomerically enriched catalyst.

A base of the α-aminosubstituted carboxylic acid amide can be converted into the associated acid addition salt using an acid, for example by reaction of equivalent amounts of the base and of the acid in an inert solvent such as ethanol and subsequent evaporation. Acids which give physiologically acceptable salts are particularly suitable for this reaction. Thus inorganic acids can be used, e.g. sulfuric acid, nitric acid, hydrohalic acids such as hydrochloric acid or hydrobromic acid, phosphoric acids such as orthophosphoric acid, sulfamic acid, furthermore organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane-or ethanesulfonic acid, p-toluenesulfonic acid, naphthalenemono- and disulfonic acids or laurylsulfuric acid. Salts with physiologically unacceptable acids, e.g. picrates, can be used for the isolation and/or purification of the compounds of the formula III.

On the other hand, α-aminosubstituted carboxylic acid amides with bases (e.g sodium or potassium hydroxide or carbonate) can be converted into the corresponding metal salts, in particular alkali metal or alkaline earth metal salts, or into the corresponding ammonium salts.

The process described herein may be conducted in any conventional reactor or in a micromixer.

In another aspect, the present invention is directed to hydroxy imino derivatives of formula IIb

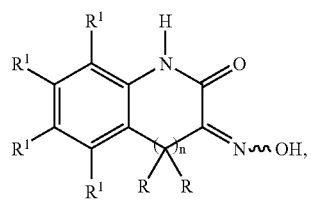

IIb in which
R is independently selected from the group consisting of H, A, —(CH$_2$)$_r$—OA, —(CH$_2$)$_r$—SA, cycloalkyl having 3 to 10 C atoms, —(CH$_2$)$_s$-cycloalkyl, fluoroalkyl having 1 to 3 C atoms, —(CH$_2$)$_r$—OAr, —(CH$_2$)$_r$—OHet, —(CH$_2$)$_s$—Ar, —(CH$_2$)$_s$—Het, NHA, NA$_2$, —(CH$_2$)$_s$—NHA or —(CH$_2$)$_s$—NA$_2$, R$^1$ is independentaly of each other H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$; NHA, NA$_2$, —(CH$_2$)$_t$—NHA, —(CH$_2$)$_t$—NA$_2$, COOH, COOA or CN, r is 2, 3 or 4,
s is 1, 2 or 3,
n is 1, 2 or 3,
t is 1, 2 or 3,
A is alkyl having 1 to 8 C atoms,
Ar is phenyl or naphthyl which are unsubstituted or mono- or disubstituted by A, OA or Hal,
Hal is F, Cl, Br or I,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF$_3$, OCF$_3$, NH$_2$, NHA, NA$_2$, COOH or COOA, and their salts.

Compounds of formula IIb are important intermediates for the production of Life Science Chemicals, particularly of pharmaceuticals or agrochemicals.

The compounds of formula IIb can exist in two isomeric forms such as formulae IV-1 and IV-2. Thus, general formula IIb includes both formulae IIb-1 and IIb-2.

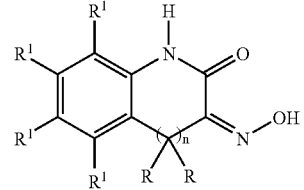

IIb-1

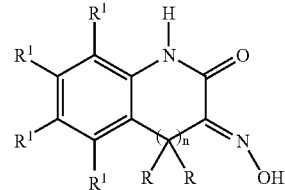

IIb-2

Particularly preferred imino derivatives are compounds of formula IIb, in which n is 2 (compounds of formula IIa)

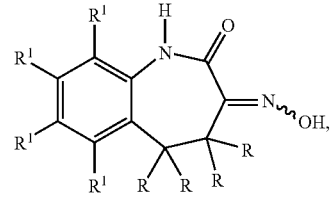

IIa and in which R and R$^1$ each independently have the meanings as indicated herein.

The invention furthermore relates to the use of compounds of the formula IIIb as defined above as intermediates for the synthesis of Life Science Chemicals, in particular of pharmaceuticals or agrochemicals. Therefore, the invention relates additionally to the use of compounds of formula IIb as intermediates for the synthesis of Life Science Chemicals, in particular of pharmaceuticals or agrochemicals.

The invention accordingly relates in particular to the use of the compounds of formula IIIb, in which n is 2 and R and $R^1$ are each independently H, for the synthesis of benazeprile. Therefore, the invention relates additionally to the use of compounds of formula IIb, in which n is 2 and R and $R^1$ are each independently H, for the synthesis of benazeprile.

In another aspect, the present invention is directed to the use of the compounds of the formula Ib in which
R is independently selected from the group consisting of H, A, —$(CH_2)_r$—OA, —$(CH_2)_r$—SA, cycloalkyl having 3 to 10 C atoms, —$(CH_2)_s$-cycloalkyl, fluoroalkyl having 1 to 3 C atoms, —$(CH_2)_r$—OAr, —$(CH_2)_r$—OHet, —$(CH_2)_s$—Ar, —$(CH_2)_s$—Het, NHA, $NA_2$, —$(CH_2)_s$—NHA or —$(CH_2)_s$—$NA_2$, $R^1$ is independentaly of each other H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —$(CH_2)_t$—OA, Het, —$(CH_2)_t$—Het, —$(CH_2)_t$—OAr, Ar, OAr, O—$CH_t$—Ar, $NO_2$, NHA, $NA_2$, —$(CH_2)_t$—NHA, —$(CH_2)_t$—$NA_2$, COOH, COOA or CN, r is 2, 3 or 4,
s is 1, 2 or 3,
n is 2,
t is 1, 2 or 3,
A is alkyl having 1 to 8 C atoms,
Ar is phenyl or naphthyl which are unsubstituted or mono- or disubstituted by A, OA or Hal,
Hal is F, Cl, Br or I,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, $CF_3$, $OCF_3$, $NH_2$, NHA, $NA_2$, COOH or COOA, according to claim 13 in nucleophilic substitution reactions.

Nucleophilic substitution reactions are well-known methods of classical organic synthesis (see on this subject standard works on organic synthesis, such as Houben-Weyl, Methoden der organischen Chemie [Methods in Organic Chemistry], Georg-Thieme-Verlag, Stuttgart, or Beyer, Walter, Lehrbuch der organischen Synthese [Handbook of Organic Synthesis], S. Hirzel Verlag, Stuttgart).

Particularly, the conversion of compounds of formula Ib into compounds of formula VIa is carried out in an inert solvent, e.g. polar aprotic solvents, in the presence of a base. Non-limiting examples of suitable bases in nucleophilic substitution reactions include hydroxides, such as sodium and potassium hydroxides; metal alkoxides, such as sodium tert.-butoxide; metal carbonates, such as potassium carbonate, cesium carbonate, and magnesium carbonate; phosphates, such as potassium phospate; alkali metal aryl oxides, such as potassium phenoxide or sodium phenoxide; alkali metal amides, such as sodium amide, including lithium amide, or tertiary amines, such as triethylamine and tributylamine.

The present invention is furthermore directed to the use of the compounds of the formula Ib in nucleophilic substitution reactions in that the compound of formula Ib is reacted with a compound of formula V $$X—R^4 \qquad V,$$

in which
X is Cl, Br, I or a reactive functionally modified OH group,
$R^4$ is A, CO—A, $CH_2$—Ar, —$(CH_2)_o$—Het, $(CH_2)_o$—OA, $(CH_2)_o$—OAr, haloalkyl having 1 to 3 C atoms, $(CH_2)_o$—$NH_2$, $(CH_2)_o$—NHA or $(CH_2)_o$—$NA_2$,
o is 1, 2, 3, 4, 5, 6 or 7,
A is alkyl having 1 to 8 C atoms,
Ar is phenyl or naphthyl which are unsubstituted or mono- or disubstituted by A, OA or Hal,
Hal is F, Cl, Br or I,
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, $CF_3$, $OCF_3$, $NH_2$, NHA, $NA_2$, COOH or COOA, in the presence of a base to form compounds of formula VIa in which R, $R^1$ and $R^4$ each independently have one of the meanings as indicated above.

X can be Cl, Br, I or a reactive functionally modified OH group, such as alkylsulfonyloxy having 1 to 6 C atoms, preferably methylsulfonyloxy, or arylsulfonyloxy having 6 to 10 C atoms, preferably phenyl- or p-tolylsulfonyloxy-1- or 2-naphthalenesulfonyloxy. X is preferentially Br or I.

Therefore, the present invention is directed additionally to compounds of the formula VIa as products of the nucleophilic substitution reaction described above, in which R is independently selected from the group consisting of H, A, —(CH$_2$)$_r$—OA, —(CH$_2$)$_r$—SA, cycloalkyl having 3 to 10 C atoms, —(CH$_2$)$_s$-cycloalkyl, fluoroalkyl having 1 to 3 C atoms, —(CH$_2$)$_r$—OAr, —(CH$_2$)$_r$—OHet, —(CH$_2$)$_s$—Ar, —(CH$_2$)$_s$—Het, NHA, NA$_2$, —(CH$_2$)$_s$—NHA or —(CH$_2$)$_s$—NA$_2$, R$^1$ is independentaly of each other H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, R$^4$ is A, CO-A, CH$_2$—Ar, —(CH$_2$)$_o$—Het, (CH$_2$)$_o$—OA, (CH$_2$)$_o$—OAr, haloalkyl having 1 to 3 C atoms, (CH$_2$)$_o$—NH$_2$, (CH$_2$)$_o$—NHA or (CH$_2$)$_o$—NA$_2$, r is 2, 3 or 4, s is 1, 2 or 3, t is 1, 2 or 3, is 1, 2, 3, 4, 5, 6 or 7, A is alkyl having 1 to 8 C atoms, Ar is phenyl or naphthyl which are unsubstituted or mono- or disubstituted by A, OA or Hal, Hal is F, Cl, Br or I, Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF$_3$, OCF$_3$, NH$_2$, NHA, NA$_2$, COOH or COOA, and their salts.

Particular preferred compounds of formula VIa are compounds, in which R and R$^1$ are each independently H and R$^4$ has one of the meanings indicated herein.

The following examples are intended to illustrate, but in no way limit the scope of the present invention.

Above and below, all temperatures are indicated in ° C.

HPLC-Assay:

| | |
|---|---|
| Column: | LiChrospher RP Select B, Cat. No.: 50839 |
| Flow: | Isocratic |
| Flow rate: | 1.0 ml/min |
| Eluate: | 35 ml acetonitrile/65 ml water, pH = 3, buffers NaH$_2$PO$_4$/H$_3$PO$_4$ |
| Detection: | UV |
| Wavelength: | 223 |
| Dosage: | Microliter |

RT = Retention Time [min]

EXAMPLE 1

1.1: Nitrosylation Reaction 5 g (31 mmol) of 1,3,4,5-tetrahydro-benzo[b]azepin-2-one (RT=5.85) is suspended in 120 ml of THF. At a temperature of −70°, 33.1 g (77,5 mmol) of n-butyllithium (15% in hexane) are added over the course of 30 min. The reaction mixture is allowed to come to room temperature and left to stir for 12 hours. Then a solution of 5, 15 g (46, 5 mmol) tert-butylnitrit in 10 ml THF is added. After the solution has been stirred for 80 hours, it is added dropwise to 150 g of a brine solution (10%) while stirring. The phases are separated and the organic phase is washed with 100 ml of 1N NaOH. The organic phase is separated off, dried over sodium sulfate and evaporated. 2,8 g (16,3 mmol) of the educt 1,3,4,5-tetrahydro-benzo[b]azepin-2-one is isolated back from the reaction mixture [53%, HPLC 94.7 area %]. The combined aqueous phases with a pH 13,0 are adjusted to pH 4,0 with 175 ml of 1N HCl and extracted three times with 100 ml dichloromethane. The combined organic phases are dried over sodium sulfate and evaporated. 2,5 g (9 mmol) of the oxime 4,5-dihydro-1H-benzo[b]azepine-2,3-dione-3-oxime is obtained [30,5%, HPLC 71,8 area %, RT=3.50, 4.10].

1.2: Reduction 5 g (26,3 mmol) of 4,5-dihydro-1H-benzo[b]azepine-2,3-dione 3-oxime is taken in 50 ml of methanol then 6,3 g (105 mmol) acetic acid is added. The reaction mixture is left to stir at 50° C. and 5 bar hydrogen pressure for 21 hours in the presence of 1,1 g Pd catalyst (5% on charcoal, containing 50% water). The reaction mixture is evaporated after filtration and the residue is dissolved in 16,5 ml water. 9,5 ml dichloromethane is added and the pH value is adjusted to pH 12–14 with NaOH (32%). After phase separation the aqueous layer is extracted two times with 5,5 ml dichloromethane each. The organic phases are dried over sodium sulfate and evaporated to give 3,12 g 3-amino-1,3,4,5-tetrahydro-benzo[b]azepin-2-one, yield 67,4%, HPLC 94,5 area %, RT=2.45.

EXAMPLE 2

2.1: Nitrosylation Reactions

The nitrosylation reactions can also be carried out under variation of the following parameters but analoguosly as described in example 1, part 1.1.

| | exp. 2.1.1. | exp. 2.1.2. | exp. 2.1.3. | exp. 2.1.4. | exp. 2.1.5. |
|---|---|---|---|---|---|
| base 1 (mole %) | — | — | KO$^t$Bu (100%) | KO$^t$Bu (100%) | — |
| solvent | THF | THF | THF | THF | THF |
| base 2, 1$^{st}$ equiv. (mole %) | LDA (310%) | sec-BuLi (300%) | n-HexLi (200%) | n-HexLi (220%) | n-HexLi (300%) |
| nitrosylating agent, 1$^{st}$ equiv. (mole %) | IPN (210%) | IPN (120%) | IPN (61%) | IPN (60%) | IPN (412%) |
| base 2, 2$^{nd}$ equiv. (mole %) | — | — | n-HexLi (100%) | n-HexLi (80%) | — |
| nitrosylating agent, 2$^{nd}$ equiv. (mole %) | — | — | IPN (62%) | IPN (60%) | — |

-continued

| | exp. 2.1.1. | exp. 2.1.2. | exp. 2.1.3. | exp. 2.1.4. | exp. 2.1.5. |
|---|---|---|---|---|---|
| yield | 48.4% | 30.2% | 43.8% | 42.2% | 25.8% |
| assay (area % HPLC) | 84.5% | 94.9% 67.1% | 90.0% | 88.0% | 99.0% 95.2% |
| additive (mole %) | — | — | — | — | TMEDA (200%) |
| notes | | 1, | 2, 3 | 2, 3 | 1, 3 |

Notes:
1 In these cases the solution of the deprotonated educt was added to a solution of the nitrosylating agent.
2 For the course of reactions with iterated additions of the base/nitrosylating agent: see example 4.
3 Extraction with ethyl acetate after acidification of the aqueous layer and treatment with active carbon before crystallization.

2.2: Reductions

The reductions can also be carried out under variation of the following parameters but analoguosly as described in example 1, part 1.2.

| | exp. 2.2.1. | exp. 2.2.2. | exp. 2.2.3. | exp. 2.2.4. |
|---|---|---|---|---|
| qty. oxime | 1 g | 1 g | 2 g | 1 g |
| solvent 1 (ml) | ethyl acetate (10 ml) | THF (10 ml) | methanol (20 ml) | methanol (50 ml) |
| solvent 2 (ml) | water (10 ml) | water (10 ml) | — | — |
| acid (mole %) | acetic acid (240%) | acetic acid (240%) | acetic acid (400%) | acetic acid (20 ml) |
| catalyst (g) | Pd/C 5% (50% $H_2O$) 0.2 g | Pd/C 5% (50% $H_2O$) 0.2 g | Raney-Ni 1.2 g in portions | Pd/C 10% 0.42 g |
| temp./press./time | 48.8° C./ 2.2 bar/1 h | 53.3° C./ 2.2 bar/2 h | 55.4° C./ 2.1/bar/58 h | 22° C./ 1/bar/20 h |
| yield assay (area % HPLC) | 99.1% conv. — | 92.8% conv. — | 75% conv. — | 88.5% 100% |
| notes | 1, 2 | 1, 2 | 1 | 2 |

Notes:
1 No workup; only monitoring by HPLC.
2 Reduction of recrystallized oxime.

EXAMPLE 3

Nucleophilic Substitution 29,01 g (0,253 mol) potassium tert-butylate is suspended in 227 ml of THF and 40 g (0,249 mol) 1,3,4,5-tetrahydrobenzo[b]azepin-2-one is added in portions at a temperature of −16°. At the same temperature 140,22 g (0,50 mol) of n-hexyllithium (33% in hexane) are added over the course of 30 min. Then a solution of 34,28 g (0,276 mol) 3-bromo propane in 21,8 ml THF is added at a temperature of −16°. After the solution has been stirred for 23 hours and meanwhile was allowed to reach room temperature, 150 g of water is added dropwise while stirring and cooling with ice water. The resulting mixture is acidified with 62 g hydrochloric acid (37%), the phases are separated and the organic phase is evaporated. 150 ml dichloromethane is added to the residue, the suspension is filtered and the filter is washed with additional 60 ml dichloromethane. The solution is concentrated and the crystals which precipitated on cooling to 0° over night are filtered off. The solid is recrystallized from 94,9 g 2-propanol. 23,3 g (0,115 mol) of 4,5-dihydro-3-(2-propyl)-1H-benzo[b]azepine-2-one is obtained [46,1%, HPLC 98,4 area %].

EXAMPLE 4

Nitrosylation Reaction 4,31 g (37,6 mmol) potassium tert-butylate is suspended in 50,35 ml of THF and 5,01 g (36,9 mmol) indoline-2-one is added at a temperature of −3°, a thick white suspension is formed and 18 ml of THF is added. Ahter cooling to −8°, 20,83 g of n-hexyllithium (33% in hexane) are added over the course of 15 min what causes an exothermic reaction. The reaction mixture is allowed to come to room temperature and left to stir for 140 minutes. Then it is cooled again to a temperature of −7° and a solution of 1,84 g (20,7 mmol) 2-propynitrit in 3,26 ml THF is added. After the solution has been stirred for 90 minutes and meanwhile reached room temperature, it is cooled again to a temperature of −8° and further 7,73 g of n-hexyllithium (33% in hexane) are added as described above. Then a solution of 1,8 g (20,2 mmol) 2-propynitrit in 2,92 ml THF is added as described above. After additional stirring for 18 hours at room temperature the reaction mixture is added to 51,93 g of water at 13°. The phases are separated and the organic phase is discarded. The aqueous phase with a pH 12,5 is adjusted to pH 3,5 with 13,72 g of 37% HCl and 323 ml ethyl. acetate are added. The aqueous layer is reextracted with 55,5 ml of ethyl acetate and the combined organic phases are dried over sodium sulfate and concentrated. The yellow solid is filtered off and dried after washig with cold ethyl acetate. 4,65 g (27,0 mmol) of the oxime indoline-2,3-dione-3-oxime is obtained [73,3%, HPLC 94,2 area %]. An analytical sample (2 g) can be recrystallized from 22,10 g water:ethanol 1:1 to yield 1,33 g indoline-2,3-dione-3-oxime [HPLC 98,92 area %, mp. 212,5°].

The invention claimed is:
1. A compound of formula IIb

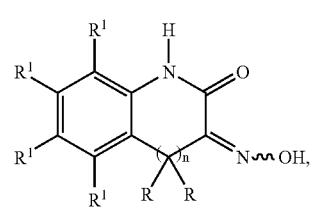

in which
R is, each independently, H, A, —$(CH_2)_r$—OA, $(CH_2)_r$—SA, cycloalkyl having 3 to 10 C atoms, —$(CH_2)_s$-cycloalkyl, fluoroalkyl having 1 to 3 C atoms, —(CH$_2$)$_r$—OAr, —(CH$_2$)$_r$—OHet, —(CH$_2$)$_s$—Ar, —(CH$_2$)$_s$—Het, NHA, NA$_2$, —(CH$_2$)$_s$—NHA or —(CH$_2$)$_s$—NA$_2$, R$^1$ is, independently of each other, H, A, OA, SA, Hal, cycloalkyl having 3 to 10 C atoms, haloalkyl having 1 to 3 C atoms, haloalkoxy having 1 to 3 C atoms, haloalkylthio having 1 to 3 C atoms, —(CH$_2$)$_t$—OA, Het, —(CH$_2$)$_t$—Het, —(CH$_2$)$_t$—OAr, Ar, OAr, O—CH$_t$—Ar, NO$_2$, NHA, NA$_2$, —(CH$_2$)$_t$—NHA, —(CH$_2$)$_t$—NA$_2$, COOH, COOA or CN, r is 2, 3 or 4,
s is 1, 2 or 3,
n is 1, 2 or 3,
t is 1, 2 or 3,
A is alkyl having 1 to 8 C atoms,
Ar is phenyl or naphthyl which are unsubstituted or mono- or disubstituted by A, OA or Hal,
Hal is F, Cl, Br or I, and
Het is a saturated, partially or completely unsaturated mono- or bicyclic heterocyclic radical having 5 to 10 ring members, where 1 or 2 N and/or 1 or 2 S or O atoms can be present and the heterocyclic radical can be mono- or disubstituted by oxo, A, Hal, OH, OA, CF$_3$, OCF$_3$, NH$_2$, NHA, NA$_2$, COOH or COOA, or a salt thereof.

2. A compound of formula IIb according to claim 1, in which n is 2.

3. A compound of formula IIb according to claim 1, in which R and R$^1$ are H.

4. A compound of formula IIb according to claim 1, in which n is 2 and R and R$^1$ are H.

* * * * *